(12) United States Patent
Yudoh

(10) Patent No.: US 8,395,037 B2
(45) Date of Patent: Mar. 12, 2013

(54) PHARMACEUTICAL COMPOSITIONS FOR TREATING/PREVENTING MOTOR ORGAN DISEASES

(75) Inventor: Kazuo Yudoh, Kawasaki (JP)

(73) Assignees: Mitsubishi Corporation, Tokyo (JP); St. Marianna University School of Medicine, Kanagawa (JP)

( * ) Notice: Subject to any disclaimer, the term of this patent is extended or adjusted under 35 U.S.C. 154(b) by 510 days.

(21) Appl. No.: 11/909,264

(22) PCT Filed: Mar. 23, 2006

(86) PCT No.: PCT/JP2006/305814
§ 371 (c)(1),
(2), (4) Date: Dec. 22, 2008

(87) PCT Pub. No.: WO2006/101163
PCT Pub. Date: Sep. 28, 2006

(65) Prior Publication Data
US 2009/0104280 A1    Apr. 23, 2009

(30) Foreign Application Priority Data
Mar. 23, 2005 (JP) .................. 2005-084051

(51) Int. Cl.
*A61K 9/14* (2006.01)
(52) U.S. Cl. ........ 977/915; 514/825; 977/734; 977/735; 977/737; 977/738; 977/904; 424/489
(58) Field of Classification Search .................. None
See application file for complete search history.

(56) References Cited

U.S. PATENT DOCUMENTS

| | | | | |
|---|---|---|---|---|
| 5,972,880 | A * | 10/1999 | Pelletier et al. | 514/16.8 |
| 5,994,410 | A * | 11/1999 | Chiang et al. | 514/709 |
| 2004/0038946 | A1* | 2/2004 | Wilson et al. | 514/102 |
| 2005/0221995 | A1 | 10/2005 | Lowe | |
| 2005/0239717 | A1* | 10/2005 | Kronholm et al. | 514/23 |
| 2006/0134095 | A1* | 6/2006 | Ito et al. | 424/125 |
| 2008/0206222 | A1 | 8/2008 | Miwa et al. | |
| 2010/0040599 | A1 | 2/2010 | Yudoh | |

FOREIGN PATENT DOCUMENTS

| | | |
|---|---|---|
| EP | 1391211 A1 | 2/2004 |
| JP | 9-227111 A | 9/1997 |
| JP | 2003-62799 A | 3/2003 |
| JP | 2006-160664 A | 6/2006 |
| WO | 01/80898 A1 | 11/2001 |
| WO | WO 02/087620 A | 11/2002 |

OTHER PUBLICATIONS

Mayoclinic osteoarthritis; [online] retrieved from: http://www.mayoclinic.com/health/osteoarthritis/DS00019/METHOD=print on Mar. 23, 2011; Nov. 24, 2010; 8 pages.*
Healia [online] retrieved from: http://www.healia.com/healthguide/guides/osteoarthritis/how-can-i-prevent-osteoarthritis on Mar. 23, 2011; Jan. 9, 2009; 1 page.*
Salter Textbook of disorder and injuries of the musculoskeletal system: 1999, Lippincott Williams & Wilkins pp. 242, 257 and 258; 5 pages.*
Mayoclinic ankylosing spondylitis; [online] retrieved from: http://www.mayoclinic.com/health/ankylosing-spondylitis/DS00483/METHOD=print on Mar. 23, 2011; Feb. 3, 2011; 5 pages.*
Wermuth, Drug Discovery today 2006, 11(7/8), pp. 348-354.*
Rice University (May 13, 1999). Fullerene-Based Materials Clear From Tissue, Go to the Bone. ScienceDaily. Retrieved Dec. 20, 2011, from http://www.sciencedaily.com /releases/1999/05/990513065619.htm. 2 pages.*
Buckwalter (Osteoarthritis, inflammation, and degradation 2007, IOS Press, pp. 31-32) 2 pages.*
Abstract of Ohira et al. (Arthritis Rheum. 1987, 30(6), 651-60) 1 page.*
Maneesh et al. (Indian Journal of Clinical Biochemistry 2005, 20(1), 129-130).*
Tumanskii et al. (Radical reactions of fullerenes and their derivatives 2001 Springer p. 186) 1 page.*
Banu, N., "Biodegradable polymers in chondrogenesis of human articular chondrocytes," *Journal of Artificial Organs*, vol. 8(3), pp. 184-191 (2005).
Tsuchiya, T., et al., "A novel promoting action of fullerene C60 on the chondrogenesis in rat embryonic limb bud cell culture system," *Biochemical and Biophysical Research Communications*, vol. 206(3), pp. 885-894 (1995).
Bensasson, R.V., et al., "Reactions of $e^-_{aq}$, $CO_2^{\cdot-}$, $HO^{\cdot}$, $O_2^{\cdot-}$ and $O_2(^1\Delta g)$ with a dendro[60]fullerene and $C_{60}[C(COOH)_2]_n$ (n = 2-6)," 2000, *Free Radic. Biol. Med.*, vol. 29(1), pp. 26-33.
Chen, H.H.C., et al., "Acute and subacute toxicity study of water-soluble polyalkylsulfonated $C_{60}$ in rats," 1998, *Toxicol. Pathol.*, vol. 26(1), pp. 143-151.
Chien, C-T, et al., "*De novo* demonstration and co-localization of free-radical production and apoptosis formation in rat kidney subjected to ischemia/reperfusion," 2001, *J. Am. Soc. Nephrol.*, vol. 12, pp. 973-982.
Chueh, S-C, et al., "Decrease of free radical level in organ perfusate by a novel water-soluble carbon-sixty, hexa(sulfobutyl)fullerenes," 1999, *Transplant. Proc.*, vol. 31, pp. 1976-1977.
Dugan, L.L., et al., "Buckminsterfullerenol free radical scavengers reduce excitotoxic and apoptotic death of cultured cortical neurons," 1996, *Neurobiol. of Dis.*, vol. 3, pp. 129-135.

(Continued)

*Primary Examiner* — Ernst Arnold
(74) *Attorney, Agent, or Firm* — Kilpatrick Townsend & Stockton LLP

(57) ABSTRACT

Fullerene inhibited the decrease in cell proliferation ability of chondrocytes which is observed when cultured chondrocytes are treated with a cartilage degenerating factor (IL-1β or $H_2O_2$). Fullerene inhibited production of cartilage matrix-degrading enzymes (matrix metalloprotease (MMP)-1, 3 and 13) which is induced in cultured chondrocytes by cartilage degenerating factors. Fullerene restored the decrease in cartilage matrix (proteoglycan) synthesizing ability which is observed in treating cultured chondrocytes with cartilage degenerating factors. In an analysis using an osteoarthritis rabbit model, the progress of cartilage degeneration was reduced by administering fullerene. Moreover, the dynamic friction coefficient was decreased by adding fullerene to synovial fluid.

10 Claims, 9 Drawing Sheets

OTHER PUBLICATIONS

Fumelli, C., et al., "Carboxyfullerenes protect human keratinocytes from ultraviolet-B-induced apoptosis," 2000, *J. Invest. Dermatol.*, vol. 115(5), pp. 835-841.

Huang, Y-L, et al., "Blockage of apoptotic signaling of transforming growth factor-β in human hepatoma cells by carboxyfullerene," 1998, *Eur. J. Biochem.*, vol. 254, pp. 38-43.

Huang, S.S., et al., "Neuroprotective effect of hexasulfobutylated $C_{60}$ on rats subjected to focal cerebral ischemia," 2001, *Free Radic. Biol. Med.*, vol. 30(6), pp. 643-649.

Huang, S.S., et al., "Effect of hexasulfobutylated $C_{60}$ on the isolated aortic ring of guinea pig," 2002, *Pharmacology*, vol. 64, pp. 91-97.

Jin, H., et al., "Polyhydroxylated $C_{60}$, fullerenols, as glutamate receptor antagonists and neuroprotective agents," 2000, *J. Neurosci. Res.*, vol. 62, pp. 600-607.

Lai, H-S, et al., "Free radical scavenging activity of fullerenol on grafts after small bowel transplantation in dogs," 2000, *Transplant. Proc.*, vol. 32, pp. 1272-1274.

Lai, H-S, et al., "Free radical scavenging activity of fullerenol on the ischemia-reperfusion intestine in dogs," 2000, *World J. Surg.*, vol. 24, pp. 450-454.

Lee, Y-T, et al., "Water-soluble hexasulfobutyl[60]fullerene inhibit low-density lipoprotein oxidation in aqueous and lipophilic phases," 2000, *Proc. Soc. Exp. Biol. Med.*, vol. 224, pp. 69-75.

Li, C., et al., "Manganese(III) acetate-mediated free radical reactions of [60]fullerene with β-dicarbonyl compounds," 2004, *Org. Biomol. Chem.*, vol. 2, pp. 3464-3469.

Lu, L-H., et al., "The possible mechanisms of the antiproliferative effect of fullerenol, polyhydroxylated $C_{60}$, on vascular smooth muscle cells," 1998, *Br. J. Pharmacol.*, vol. 123, pp. 1097-1102.

Mirkov, S.M., et al., "Nitric oxide-scavenging activity of polyhydroxylated fullerenol, $C_{60}(OH)_{24}$," 2004, *Nitric Oxide*, vol. 11, pp. 201-207.

Miura, Kouji and Diasuke Tsuda. "Superlubicity of $C_{60}$ intercalated graphite films," 2005, *e-J. Surf. Sci. Nanotech.*, vol. 3, pp. 21-23.

Miura, K., et al., "$C_{60}$ molecular bearings," 2003, *Phys. Rev. Lett.*, vol. 90(5), pp. 055509-1 to 055509-4.

Murayama. "Jikososhikika ni yoru nanomaterial no sousei to ouyou [Creation and application of nanomaterials by means of self-organization]," In *Self-organization in nanocarbon materials*, 2004, pp. 153-178.

Satoh, M., et al., "Inhibitory effects of a fullerene derivative, dimalonic acid $C_{60}$, on nitric oxide-induced relaxation of rabbit aorta," 1997, *Eur. J. Pharmacol.*, vol. 327, pp. 175-181.

Satoh, M., et al., "Inhibitory effect of a fullerene derivative, monomalonic acid $C_{60}$, on nitric oxide-dependent relaxation of aortic smooth muscle," 1997, *Gen. Pharmacol.*, vol. 29(3), pp. 345-351.

Tsai, M-C, et al., "Polyhydroxylated $C_{60}$, fullerenol, a novel free-radical trapper, prevented hydrogen peroxide- and cumene hydroperoxide-elicited changes in rat hippocampus in-vitro," 1997, *J. Pharm. Pharmacol.*, vol. 49, pp. 438-445.

Wang, I.C., et al., "$C_{60}$ and water-soluble fullerene derivatives as antioxidants against radical-initiated lipid peroxidation," 1999, *J. Med. Chem.*, vol. 42, pp. 4614-4620.

Wei, Y., et al., "Studies on electrochemical properties and scavenge of superoxide anion in aprotic media by using carbon nanotubes powder microelectrode," 2003, *Bioelectrochemistry*, vol. 61, pp. 51-56.

Wolff, D.J., et al., "Inhibition of nitric oxide synthase isoforms by tris-malonyl-$C_{60}$-fullerene adducts," 2000, *Arch. Biochem. Biophys.*, vol. 378(2), pp. 216-223.

Wolff, D.J., et al., "Trisamine $C_{60}$-fullerene adducts inhibit neuronal nitric oxide synthase by acting as highly potent calmodulin antagonists," 2002, *Arch. Biochem. Biophys.*, vol. 399(2), pp. 130-141.

Wolff, D.J., et al., "$C_{60}$-fullerene monomalonate adducts selectively inactivate neuronal nitric oxide synthase by uncoupling the formation of reactive oxygen intermediates from nitric oxide production," 2001, *Biochemistry*, vol. 40, pp. 37-45.

Yamakoshi, Y., et al., "Active oxygen species generated from photoexcited fullerene ($C_{60}$) as potential medicines: $O_2^{\bullet-}$ versus $O_2$," 2003, *J. Am. Chem. Soc.*, vol. 125, pp. 12803-12809.

Zhang, T-H, et al., "Reaction of [60]fullerene with free radicals generated methylene compounds by manganese(III) acetate dihydrate," 2003, *Org. Biomol. Chem.*, vol. 1, pp. 4403-4407.

Bosi, et al., "Fullerene derivatives: an attractive tool for biological applications," *Eur J Med Chem.*, vol. 38(11-12), pp. 913-923 (Nov. 2003-Dec. 2003).

* cited by examiner

PHARMACEUTICAL COMPOSITIONS FOR TREATING/PREVENTING MOTOR ORGAN DISEASES

CROSS-REFERENCES TO RELATED APPLICATIONS

This application is a U.S. National Stage Application of PCT/JP2006/305814, filed Mar. 23, 2006, which claims the benefit of Japanese Patent Application No. 2005-084051 filed Mar. 23, 2005, all of which are hereby incorporated by reference in their entirety.

TECHNICAL FIELD

The present invention relates to pharmaceutical agents capable of inhibiting the production of cartilage matrix-degrading enzymes involved with oxidative stress and the like, and capable of inhibiting decrease of cartilage matrix-synthesizing ability, particularly, pharmaceutical agents comprising fullerene. Moreover, the present invention relates to pharmaceutical compositions comprising fullerene for treating/preventing motor organ diseases involving cartilage degenerations such as osteoarthritis.

BACKGROUND ART

With the arrival of an aging society, the development of countermeasures and preventive methods against bone and joint diseases/motor organ diseases such as osteoarthritis has been attracting attention as an urgent social task. In Japan, the estimated number of osteoporosis patients is about ten million, and the estimated number of osteoarthritis patients is seven to ten million. The number of patients having impairments that affect daily life tends to increase year by year. Most of the treatments of joint diseases/motor organ diseases are guidance for improving daily movements (muscle exercises, use of supporters/braces, and the like) and symptomatic therapies using anti-inflammatory analgesic agents, efficacies of which are not satisfactory. Articular symptoms worsen with age, and surgical treatments (using artificial joints and the like) are being selected for cases with osteoarticular destruction or alignment irregularities. However, these surgical treatments have many issues such as cost and infection, and furthermore, some patients are forced to replace their artificial joints after several years or several decades due to longevity.

Preventive methods and early countermeasures are required for motor organ diseases since tissues get damaged with time following disease onset, and articular cartilage tissues are extremely poor in repairability. However, neither effective treatments nor medical techniques have yet been established. Therefore, the establishment of novel pharmaceutical agents and therapeutic strategies showing a clinical efficacy against age-related motor organ diseases is urgently needed to maintain high activities of daily living (ADL) in an aging society.

In the process of bone and joint disease formation, deterioration of bone/chondrocyte environment (degeneration of osteocartilaginous matrix caused by external stress, following enzymatic degradation, inflammation, immune response, and the like) decreases the homeostasis/repairability of osteoarticular tissues, and articular degeneration/destruction progresses with time. Among inducers of motor organ diseases, oxygen free radicals (oxidative stress) are most important. All somatic cells produce reactive oxygen species during the process of cellular respiration (mitochondrial respiratory chain function: energy production), which is the root of vital activity. Decrease of cellular respiratory chain function and antioxidative enzyme activity due to aging and various external stresses, cause excessive reactive oxygen (oxygen free radicals), and are suggested to be closely associated with etiologic factors/pathological conditions of diseases involved with aging such as degenerative diseases and cancers.

Fullerene (C60) is a nano-carbon material that inhibits generation/leakage of reactive oxygen species. Fullerene (C60) has been suggested to have a strong free radical capturing/scavenging ability, and to have effects of regulating the cellular environment against various cellular catabolisms (cellular function/activity decrease, cell death), and maintaining and enhancing cellular functions (Non-Patent Documents 1 to 27).

Moreover, super-lubricating systems with no dynamic friction that utilize molecular motions of fullerene have been recently developed, and fullerene is expected to be applied as a lubricant for micro/nanomachines and the like (Patent Document 1 and Non-Patent Document 28). Fullerene constantly rotates by Brownian motion, and super-lubricating systems with a close-to-zero dynamic friction coefficient due to the rotation actions of fullerene molecules have been observed. This suggests that fullerene can become a lubricant with an extremely high performance.

Patent Document 1: Japanese Patent Application Kokai Publication No. 2003-06279 (unexamined, published Japanese patent application)
Non-Patent Document 1: Li C, et al., Org Biomol Chem. 2004 Dec. 7, 2(23):3464-9
Non-Patent Document 2: Mirkov S M, et al., Nitric Oxide. 2004 September, 11(2):201-7
Non-Patent Document 3: Zhang T H, et al., Org Biomol Chem. 2003 Dec. 21, 1(24):4403-7
Non-Patent Document 4: Wei Y, et al., Bioelectrochemistry. 2003 October, 61(1-2):51-6
Non-Patent Document 5: Yamakoshi Y, et al., J Am Chem Soc. 2003 Oct. 22, 125(42):12803-9
Non-Patent Document 6: Wolff D J, et al., Arch Biochem Biophys. 2002 Mar. 15, 399(2):130-41
Non-Patent Document 7: Huang S S, et al., Pharmacology. 2002 February, 64(2):91-7
Non-Patent Document 8: Chien C T, et al., J Am Soc Nephrol. 2001 May, 12(5):973-82
Non-Patent Document 9: Wolff D J, et al., Biochemistry. 2001 Jan. 9, 40(1):37-45
Non-Patent Document 10: Jin H, et al., J Neurosci Res. 2000 Nov. 15, 62(4):600-7
Non-Patent Document 11: Fumelli C, et al., J Invest Dermatol. 2000 November, 115(5):835-41
Non-Patent Document 12: Lai H S, et al., Transplant Proc. 2000 September, 32(6):1272-4
Non-Patent Document 13: Bensasson R V, et al., Free Radic Biol Med. 2000 Jul. 1, 29(1):26-33
Non-Patent Document 14: Wolff D J, et al., Arch Biochem Biophys. 2000 Jun. 15, 378(2):216-23
Non-Patent Document 15: Lee Y T, et al., Proc Soc Exp Biol Med. 2000 June, 224(2):69-75
Non-Patent Document 16: Lai H S, et al., World J Surg. 2000 April, 24(4):450-4
Non-Patent Document 17: Wang I C, et al., J Med Chem. 1999 Nov. 4, 42(22):4614-20
Non-Patent Document 18: Chueh S C, et al., Transplant Proc. 1999 August, 31(5):1976-7
Non-Patent Document 19: Huang Y L, et al., Eur J Biochem. 1998 May 15, 254(1):38-43

Non-Patent Document 20: Lu L H, et al., Br J Pharmacol. 1998 March, 123(6):1097-102

Non-Patent Document 21: Chen H H, et al., Toxicol Pathol. 1998 January-February, 26(1):143-51

Non-Patent Document 22: Satoh M, et al., Gen Pharmacol. 1997 September, 29(3):345-51

Non-Patent Document 23: Satoh M, et al., Eur J Pharmacol. 1997 May 30, 327(2-3):175-81

Non-Patent Document 24: Tsai M C, et al., J Pharm Pharmacol. 1997 April, 49(4):438-45

Non-Patent Document 25: Dugan L L, et al., Neurobiol Dis. 1996, 3(2):129-35

Non-Patent Document 26: Huang S S, et al., Free Radic Biol Med. 2001 Mar. 15, 30(6):643-9

Non-Patent Document 27: Publisher, Takashi Yoshida; NTS Co.; Creation and Application of Nano-materials by means of Self-Organization, Sixth lecture "Self-Organization in Nano-Carbon Materials" 153-178, 2004

Non-Patent Document 28: Superlubricty of C60 Intercalated Graphite Films. Kouji Miura and Daisuke Tsuda, e-J. Surf. Sci. Nanotech. Vol. 3 (2005) 21-23, C60 Molecular Bearings. K. Miura, S. Kamiya and N. Sasaki, Physical Review Letters, Vol. 90, No. 5, 055509 (2003)

DISCLOSURE OF THE INVENTION

Problems to be Solved by the Invention

The present inventor has so far revealed that primary and secondary stress generated in response to various internal/external factors give rise to genome destabilization in osteoarticular tissues, which is associated with decrease of the activity, life span and functions of articular component cells. If the generation/leakage of reactive oxygen species associated with such disease formation can be inhibited in motor organs that are important for maintaining daily activities, it will be possible to develop new therapeutic agents and treatment devices for motor organ diseases which currently have no effective preventive/therapeutic method.

Therefore, an objective of the present invention is to provide novel preventive/therapeutic agents for motor organ diseases associated with generation of reactive oxygen species.

Means for Solving the Problems

In view of the above problems, the present inventor focused on the abovementioned nano-carbon material, fullerene, and conducted dedicated studies on whether fullerene has a therapeutic effect on osteoarthritis (cartilage degeneration). As a result, the present inventor discovered that fullerene has a therapeutic effect on cartilage degeneration in an experimental culture system and also in a research using an osteoarthritis rabbit model. Specifically, hydroxylated fullerene inhibited decrease of chondrocyte-proliferation ability observed when cultured chondrocytes are treated with cartilage degenerating factors (IL-1β and $H_2O_2$). When cultured chondrocytes are treated with cartilage degenerating factors, matrix metalloprotease (MMP)-1, 3, and 13, which are cartilage matrix-degrading enzymes, are produced; however, the addition of hydroxylated fullerene inhibited the production of all of MMP-1, 3 and 13. When cultured chondrocytes are treated with cartilage degenerating factors, the cartilage matrix (proteoglycan) synthesizing ability decreases, but this ability was restored by the addition of hydroxylated fullerene. Moreover, the progress of cartilage degeneration was relieved compared to the control group when hydroxylated fullerene was injected into joints of an osteoarthritis rabbit model whose joint ligaments had been excised. Furthermore, hypothesizing that fullerene has a protective effect (effect of maintaining/improving the low friction of articular cartilages and the lubricating ability of synovial fluid) on joint sliding surfaces of articular tissue joints, fullerene was added to osteoarthritis patient-derived synovial fluid, a 50% polyethylene glycol solution, and a joint function-improving agent (hyaluronic acid formulation), and their dynamic friction coefficients were measured to compare with when fullerene was not added. As a result, fullerene addition decreased the dynamic friction coefficients in all of these solutions. From these results, it was discovered that fullerene can be utilized as a preventive and therapeutic agent targeting motor organs (bones and joints) affected by osteoarthritis diseases which currently have no effective therapeutic methods, at a relatively early to middle stage (from an early stage up to an advanced stage) following disease onset, and the present invention was completed. That is, the present invention is as shown below:

[1] an inhibitory agent against production of a cartilage matrix-degrading enzyme, comprising at least one selected from the group consisting of a fullerene, a clathrate fullerene, a fullerene derivative, and a salt thereof;

[2] the inhibitory agent against production of a cartilage matrix-degrading enzyme of [1], wherein the cartilage matrix-degrading enzyme is a matrix metalloprotease induced by a cartilage degenerating factor in a chondrocyte;

[3] the inhibitory agent against production of a cartilage matrix-degrading enzyme of [1], wherein the cartilage matrix-degrading enzyme is MMP-1, 3, and/or 13;

[4] an inductive agent for cartilage matrix production, comprising at least one selected from the group consisting of a fullerene, a clathrate fullerene, a fullerene derivative, and a salt thereof;

[5] the inductive agent for cartilage matrix production of [4], wherein the agent is for a cartilage matrix whose production has been decreased by a cartilage degenerating factor in a chondrocyte;

[6] the inductive agent for cartilage matrix production of [4], wherein the cartilage matrix is proteoglycan and/or type II collagen;

[7] a preventive/therapeutic agent for a motor organ disease, comprising at least one selected from the group consisting of a fullerene, a clathrate fullerene, a fullerene derivative, and a salt thereof, as an active ingredient;

[8] a preventive/therapeutic agent for a motor organ disease, comprising at least one selected from the group consisting of C60 fullerene, clathrate C60 fullerene, a C60 derivative, and a salt thereof, as an active ingredient;

[9] a preventive/therapeutic agent for a motor organ disease, comprising hydroxylated C60 fullerene as an active ingredient;

[10] the therapeutic/preventive pharmaceutical composition of any one of [7] to [9], wherein the motor organ disease is a motor organ disease associated with oxidative stress;

[11] the therapeutic/preventive pharmaceutical composition of any one of [7] to [9], wherein the motor organ disease is a disease involving cartilage degeneration;

[12] the therapeutic/preventive pharmaceutical composition of any one of [7] to [9], wherein the motor organ disease is osteoarthritis;

[13] a method for producing a preventive/therapeutic agent for a motor organ disease, comprising the step of mixing at least one selected from the group consisting of a fullerene, a clathrate fullerene, a fullerene derivative, and a salt thereof, with a compounding agent; and

[14] a method for preventing or treating a motor organ disease, using at least one selected from the group consisting of a fullerene, a clathrate fullerene, a fullerene derivative, and a salt thereof.

BEST MODE FOR CARRYING OUT THE INVENTION

Figure 1:
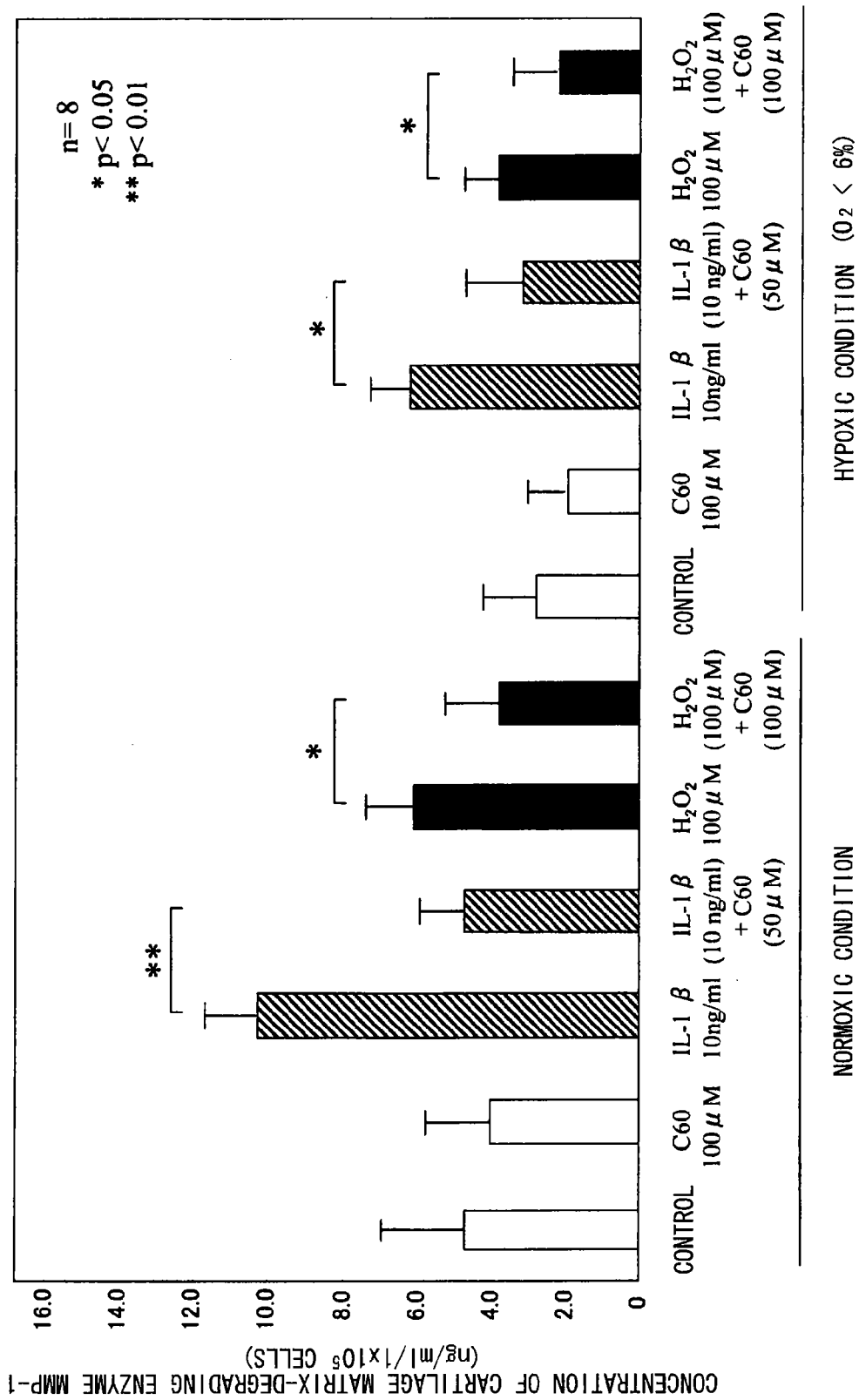
FIG. 1 is a histogram showing that the amount of produced cartilage-degrading enzyme MMP-1 differs depending on the presence/absence of fullerene when cultured chondrocytes are treated with a cartilage degenerating factor (IL-1β or $H_2O_2$). The addition of fullerene decreased the amount of MMP-1 produced, which had been increased by the cartilage degenerating factor.

First, the present invention provides pharmaceutical agents which inhibit the biological activities in chondrocytes capable of inducing cartilage degeneration, utilizing fullerenes, clathrate fullerenes, fullerene derivatives, and salts thereof (hereinbelow, may be called "fullerenes" in the present description). Fullerene is typically a molecule having a closed pseudo-spherical structure in which each of the 20 or more carbon atoms is bound to the adjacent three atoms. The known numbers of carbon atoms are 60, 70, 76, 78, and the like. In the present invention, any one of these fullerenes such as C60 and C70 can be suitably used, as long as it has an activity capable of scavenging reactive oxygen, or as long as it has a protective effect on a sliding surface of a joint. Moreover, fullerene derivatives such as heterofullerene, norfullerene, homofullerene, secofullerene, chemically modified fullerenes, fullerene polymers, and salts thereof can also be suitably used, as long as they have the abovementioned activity or effect. Chemical modifications include hydrogenation and addition of substituents to fullerene. Examples of substituents that can be added to fullerene include hydroxyl groups, but are not specifically limited thereto as long as the reactive oxygen scavenging ability of fullerene can be retained and cytotoxicity can be kept low. Moreover, the proportion of the additional substituents to carbons can be appropriately adjusted considering the reactive oxygen scavenging ability and influence on cytotoxicity. Besides modification using substituents, modification using hydrophilic high molecules and the like may be performed to improve fullerene compatibility with cells and tissues. Examples of such hydrophilic high molecules include polyethylene glycol, hyaluronic acid, and the like.

Fullerene is normally hydrophobic, and is poorly soluble in water. Therefore, fullerene may be made hydrophilic (water-solubilized) and used for the sake of formulation convenience or the like, when fullerene is used as an agent of the present invention. Examples of means for water-solubilizing fullerene include the addition of hydrophilic substituents such as a hydroxyl group, an amino group, and a carboxyl group. Hydroxylated fullerenes are examples of hydrophilic fullerenes that can be suitably used. Specific examples of commercially available hydroxylated fullerenes include "Nanom Spectra" manufactured by Frontier Carbon Corporation.

Moreover, other means for water-solubilizing fullerene include clathration with water-soluble high molecules (such as polyvinyl pyrrolidone (PVP)) or water-soluble macrocyclic compounds (such as cyclodextrin). Such clathrated fullerenes (clathrate fullerenes) are one of the "fullerenes" that are suitably used as an agent of the present invention.

As a method for measuring the cytotoxicity of fullerenes, the XTT method shown in Example 1(2) described later may be used, for example. Moreover, the reactive oxygen scavenging ability of fullerenes with modifications and the like, may be measured by methods for measuring the antioxidative ability of the fullerenes, an example of which includes the method using copper ion-reducing power as an index (Schitt A A, Pergamon Press, London, Newwork, Paris, 1966, Yamanishi N et al., Alpha-tocopherol induces oxidative damage to DNA in the presence of copper (II) ions. Chemical Res. Toxicl. 11:855-858, 1998), or the like. Specifically, evaluation can be performed by contacting $Cu^{2+}$ ions and a fullerene, and using as an index, whether the reduction reaction from $Cu^{2+}$ into $Cu^+$ can be inhibited (copper ion-reducing power). In addition, the reactive oxygen scavenging ability of fullerenes may be measured by antioxidative ability evaluation methods which utilize weak luminescence emitting when reactive oxygen (hydrogen peroxide) reacts with an antioxidant (Y) (weak luminescence spectrometry for analyzing reactive oxygen scavenging), analytical methods for superoxide scavenging activity (SOD-like activity), or the like.

The present inventor has discovered that the above-mentioned fullerenes improve various biological activities in chondrocytes which are capable of inducing cartilage degeneration caused by oxidative stress. One of these biological activities is the production of cartilage matrix-degrading enzymes. When chondrocytes receive oxidative stress, the production of cartilage matrix-degrading enzymes is increased in chondrocytes. This increase in the production of cartilage matrix-degrading enzymes causes cartilage matrix degeneration in joints and the like, and gives rise to motor organ diseases such as osteoarthritis. Agents comprising fullerene of the present invention can inhibit such production of cartilage matrix-degrading enzymes caused by oxidative stress. Therefore, a first aspect of the present invention is to provide agents comprising fullerenes, which agents inhibit the production of cartilage matrix-degrading enzymes.

The term "oxidative stress" which induces the production of cartilage matrix-degrading enzymes refers to stress on chondrocytes caused not only by direct reactive oxygen species such as hydrogen peroxide but also by reactive oxygen species indirectly generated by cartilage degenerating factors such as IL-1β, mechanical stimuli to articular cartilages, and the like. Agents comprising fullerenes of the present invention are capable of inhibiting the production of cartilage matrix-degrading enzymes which is induced by both of these direct oxidative stress and oxidative stress indirectly generated by cartilage degenerating factors and mechanical stimuli.

Moreover, the term "cartilage matrix-degrading enzyme" includes enzymes which induce oxidative stress-induced degradation of cartilage matrix, specific examples being matrix metalloprotease (MMP)-1, 3, and 13. These enzymes are main degrading enzymes of type II collagen which is the main component collagen of cartilage matrix.

If a fullerene is used as an inhibitory agent against the production of cartilage matrix-degrading enzymes, concentration of the fullerene can be appropriately determined according to the fullerene type. For example, concentration of hydroxylated C60 fullerene may be 0.1 µM to 1000 µM, preferably 10 µM to 200 µM, and more preferably 10 µM to 100 µM. Optimum concentrations of other fullerenes may be examined according to the method shown in Example 1(3).

Moreover, a solvent for dissolving a fullerene, which is used when chondrocytes are treated with the fullerene, may be any solvent as long as it does not negatively affect cells and the inhibitory activity on the production of cartilage-degrading enzymes, and may be appropriately selected from buffer solutions, polyethylene glycol solutions, hyaluronic acid solutions, and the like, for use.

A second aspect of the present invention is to provide cartilage matrix synthesis-promoting agents comprising fullerenes. That is, this present invention is based on the finding that fullerenes have the capability of improving cartilage matrix-synthesizing ability decreased due to oxidative stress, as another novel biological activity of fullerenes. When chondrocytes receive oxidative stress as mentioned above, the cartilage matrix-synthesizing ability is decreased; however the fullerenes can improve this decreased cartilage matrix-synthesizing ability. The "cartilage matrix", which is a subject of the present invention, refers to cartilage matrices whose synthesizing ability is decreased by oxidative stress, such as type II collagens, glucosaminoglycans, and proteoglycans. Glucosaminoglycans composed of polysaccharides such as chondroitin sulfate, keratan sulfate, heparin, and heparan sulfate are further covalently bound with proteins to form proteoglycans having a high-order molecular structure. Both of these glucosaminoglycans and proteoglycans fill the space between collagen fibers, or are crosslinked to constitute cartilage matrix.

Agents of the present invention are capable of inducing the cartilage matrix synthesis mentioned above. The term "oxidative stress" which decreases cartilage matrix synthesis includes oxidative stress applied to chondrocytes not only by direct reactive oxygen species such as hydrogen peroxide but also by reactive oxygen species indirectly generated by cartilage degenerating factors, mechanical stimuli applied to joints, and the like.

If a fullerene is used as a promoting agent for cartilage matrix synthesis, concentration of the fullerene can be appropriately determined according to the fullerene type. For example, concentration of hydroxylated C60 fullerene may be 0.1 µM to 1000 µM, preferably 10 µM to 200 µM, and more preferably 10 µM to 100 µM. Optimum concentrations of other fullerenes may be examined according to the method shown in Example 1(4). Moreover, a solvent that can be used for dissolving a fullerene when chondrocytes are treated with the fullerene may be, as described above, appropriately selected from buffer solutions, polyethylene glycol solutions, hyaluronic acid solutions, and the like, for use.

A third aspect of the present invention is to provide pharmaceutical compositions for treating/preventing motor organ diseases involving oxidative stress. Various motor organ diseases occur when cartilage cells/tissues are deformed by oxidative stress. The pharmaceutical compositions of the present invention attempt the treatment/prevention of motor organ diseases by inhibiting the deformation of cartilage cells/tissues or promoting the cartilage matrix synthesis mentioned above, or by improving the low friction of articular cartilages and the lubricating ability of synovial fluid, with the aid of fullerenes. The "motor organ diseases", which are subjects of treatment/prevention in the present invention, refer to motor organ diseases induced by oxidative stress, more specifically, motor organ diseases associated with deformation of cartilage cells/tissues and cartilage matrix-synthesizing ability decrease due to oxidative stress. That is, the subject can be a motor organ disease in which a bone, tendon, or muscle is damaged due to the deformation of cartilage cells/tissues caused by oxidative stress. Such motor organ diseases include osteoarthritis, osteoarthritis of spine, arthritis involving cartilage degeneration in rheumatic diseases, and the like.

Fullerenes used as therapeutic agents for motor organ diseases of the present invention desirably have an inhibitory effect on the production of cartilage matrix-degrading enzymes or an inductive effect on the production of cartilage matrix, or are expected to have an effect of maintaining/improving the low friction of articular cartilages or the lubricating ability of synovial fluid. Whether a fullerene has an inhibitory effect on the production of cartilage matrix-degrading enzymes or an inductive effect on the production of cartilage matrix, can be determined by the above method. Whether a certain fullerene can be expected to have an effect of maintaining/improving the low friction of articular cartilages or a lubricating ability of synovial fluid can be determined by the method mentioned in Example 3 described later. Furthermore, considering biocompatibility, hydrophilic fullerenes are preferably used for fullerenes used in therapeutic agents for motor organ diseases of the present invention. Examples of the hydrophilic fullerenes are as described above. Preferable hydrophilic fullerenes include hydroxylated fullerenes, and hydroxylated C60 fullerene is more preferable. In addition to functional groups such as hydroxyl groups, a fullerene may hold optional materials which are useful for the treatment of motor organ diseases. These materials are not specifically limited, and may be a low molecule compound, a high molecule polymer, a protein, a nucleic acid, and the like.

As described above, fullerenes may be used to produce pharmaceutical compositions for treating or preventing motor organ diseases. If a fullerene is used as an active ingredient of pharmaceutical compositions for treating motor organ diseases, the fullerene may be appropriately mixed with suitable additives and formulated via various processes. The additives used for preparing formulations may be selected from pharmaceutically acceptable additives according to the purposes. "Pharmaceutically acceptable additives" include excipients, diluents, extenders, disintegrators, stabilizers, preservatives, buffering agents, emulsifiers, aromatic substances, colorants, sweeteners, thickening agents, flavoring agents, solubilizing agents, and other additives. A fullerene can be formed into a pharmaceutical composition for treating motor organ diseases by mixing directly with various additives, or by mixing with them after dissolving the fullerene in an appropriate solvent, and subjecting to various processes such as granulation, sorting, kneading, shaping, drying, tablet-making, packing, sterilization, and aseptic filtration, according to the desired form of formulation. Formulation of pharmaceutical compositions according to the present invention may be in any form such as oral agents (tablets, granules, solutions, capsules, and the like), injections, patches, liniments, suspensions, emulsions, or ointments, as long as the form allows the composition to reach an affected part. However, injections and the like which can be directly injected into an affected part are preferable, as a method that reliably delivers an agent to an affected part. Injections, for example, can be produced by dissolving, suspending, or emulsifying fullerene in a pharmaceutically acceptable carrier to meet the dosage described below. As a carrier used for injections, non-aqueous diluents (such as propylene glycol, polyethylene glycol, vegetable oil such as olive oil, and alcohols such as ethanol) may be adopted as well as physiological salt solutions or commercially available distilled water for injection. The injections can be sterilized by filter sterilization using a bacteria-retaining filter, by mixing disinfectants, or by irradiation. The injections can be produced in a form that allows preparation when needed. That is, sterile fullerenes prepared by lyophilization and the like, can be used by dissolving in a sterile carrier before use.

Moreover, dosage of pharmaceutical compositions of the present invention can be appropriately determined according to the condition, size and the like of the affected part; the dosage can be 0.1 µM to 1000 µM, preferably 10 µM to 200 µM, and more preferably 10 µM to 100 µM per affected part. Since the dosage varies according to various conditions, amounts smaller than the above dosage may be sufficient in some cases, and dosages over the above range may be required in other cases.

The present invention provides novel agents that can treat/prevent motor organ diseases involving deformation of cartilage matrix. The therapeutic/preventive agents for motor organ diseases of the present invention attempt the treatment/prevention by inhibiting the progress of cartilage cell/tissue deformations in affected parts, or promoting cartilage matrix synthesis. Accordingly, they are effective as therapeutic agents for motor organ diseases such as osteoarthritis from an early stage to an advanced stage.

All prior art documents cited in the present specification are incorporated herein by reference.

EXAMPLES

Example 1

Influence on Cultured Chondrocytes

The inhibitory effect of fullerenes having a strong oxidative stress (oxygen free radical) scavenging ability on motor organ degeneration was examined from the viewpoint of cell biology/pharmacology.

(1) Culture of Osteoarthritis Patient-Derived Chondrocytes

Chondrocytes isolated from human articular cartilage tissues were used for cultured cells. After obtaining informed consent, cartilage tissues were collected from surgically-removed tissues from eight osteoarthritis patients. The collected tissues were sliced and then treated in a liquid low-glucose Dulbecco's modified Eagle's medium (DMEM, manufactured by Gibco Co.) containing 1.5 mg/ml collagenase B at 37° C. overnight, to isolate chondrocytes for culture. The cells were normally cultured in a culture flask (culture area: 25 cm$^2$), and in a polystyrene culture dish (diameter: 6 cm) for use in the experiments. The cell culture was performed using a DMEM medium added with inactivated fetal bovine serum (FBS, manufactured by TRACE Co.) at 10% volume of the medium, and also 2 mM L-glutamine, 25 mM HEPES, and penicillin and streptomycin at 100 units/ml, in either a $CO_2$ incubator (normoxic condition) which was set at 5% $CO_2$+95% air, or a low oxygen chamber (hypoxic condition) which was set at 1% $O_2$+5% $CO_2$+94% $N_2$, at 37° C. under saturated humidity.

For passagging, the cells were washed with a phosphate buffer solution (PBS, manufactured by Nissui Co.) and then peeled off using a 0.25% trypsin-PBS solution (Gibco Co.), and then dispersed by pipetting and diluted with the medium to an appropriate concentration.

(2) Test of Hydroxylated C60 Fullerene Cytotoxicity to Chondrocytes

Influence of hydroxylated C60 fullerene on the survival rate of chondrocytes was evaluated by a cytotoxicity test (XTT method). Hydroxylated C60 fullerene (manufactured by Frontier Carbon Co.) was dissolved in polyethylene glycol to prepare a 10 mM stock, which was then stored in a dark place at −20° C. The concentration of hydroxylated C60 fullerene for the test was 1.0 µM, 10.0 µM, and 100.0 µM.

50 µl each of chondrocytes in the logarithmic growth phase were added into a 96-well microplate at the concentration of 5.0×10$^5$ cells/ml, and incubated in either a $CO_2$ incubator (normoxic condition) or a low oxygen chamber (hypoxic condition) for 24 hours. Hydroxylated C60 fullerene was added into the 96-well microplate at each target concentration described above (final volume: 100 µl), and the cells were incubated for 48 hours or 96 hours. Then, the medium was replaced to remove hydroxylated C60 fullerene, and the cells were incubated for another 12 hours. To stain surviving cells, 50 µl XTT (2,3bis(2-methoxy-4-nitro-5-sulfophenyl)-5-[(phenylamino)carbonyl]-2H-tetrazolium hydroxide, inner salt) reagent was added to each well, and the cells were incubated for four hours. Immediately thereafter, the absorbance at 450 nM was measured with a plate reader and the cell survival rates were analyzed. The results are shown as survival rates. The survival rate of the control group in a medium alone without hydroxylated C60 fullerene was assumed to be 100%, and the survival rate of the hydroxylated C60 fullerene-administered groups is expressed as relative values against the control group.

TABLE 1

| | Cell survival rate (%) | | | |
| --- | --- | --- | --- | --- |
| | Control | Hydroxylated fullerene (µM) | | |
| | (medium alone) | 1.0 | 10.0 | 100.0 |
| 48 hour incubation | 100.0 | 98.5 ± 6.5 | 101.3 ± 5.8 | 99.5 ± 4.2 |
| 96 hour incubation | 100.0 | 99.6 ± 3.8 | 98.2 ± 2.6 | 103.4 ± 2.2 |

Even in the cases where the cells were treated with each concentration of hydroxylated C60 fullerene for 48 hours or 96 hours, the obtained survival rates were equivalent to that of the control group. From these results, hydroxylated C60 fullerene was shown not to be toxic to chondrocytes.

(3) Mitigating Effect of Hydroxylated C60 Fullerene on the Production of Cartilage Matrix-Degrading Enzymes Influence of hydroxylated C60 fullerene on cartilage matrix-degrading enzyme production which is enhanced by cartilage catabolism inducers was analyzed using the enzyme-linked immunoassay (ELISA) method.

Chondrocytes that had been isolated and cultured by the above method (1) were subjected to two passage cultures. Then, these cells in a subconfluent state were disseminated into a 24 well-culture plate at $1 \times 10^5$ cells/well. After incubation for 12 hours, the wells were washed with PBS and the medium was replaced with a fresh 10% FBS-containing DMEM. A cartilage catabolism inducer (either 10.0 ng/ml interleukin (IL)-1β, or 100 µM hydrogen peroxide solution ($H_2O_2$, purchased from Wako Pure Chemical Industries, Ltd.)), and 50.0 µM or 100.0 µM hydroxylated C60 fullerene were added to cultured cells. The plate was incubated for 24 hours. As controls, experiments of a group cultured in medium alone and groups cultured in the medium added only with either (IL)-1β or hydrogen peroxide solution were conducted in parallel. After a 24 hour incubation, the culture supernatant was collected, and the concentrations of cartilage matrix-degrading enzymes, matrix metalloprotease (MMP)-1, 3, and 13, were measured.

The concentrations of MMP-1, MMP-3, and MMP-13 in the culture supernatant were determined using ELISA kits (kits for MMP-1 and MMP-3, manufactured by R&D Co.; and a kit for MMP-13, manufactured by Amersham), which is the standard technique currently known in the art. The ELISA was performed by the following standard method: the diluted culture supernatant sample was added into a sensitized plate at 100 µl per well, and the plate was left still for one hour at room temperature (primary reaction). After the primary reaction, the wells were sufficiently washed with PBS using a wash bottle four times or more. Horseradish peroxidase (HRP)-labeled goat anti-rabbit IgG (H+L) antibodies that have been diluted 3,000-folds with 0.1% Tween 20-PBS were dispensed into the respective wells at 100 µl each, and the plate was left still for one hour at room temperature (secondary reaction). After the secondary reaction, the wells were washed with PBS in the same manner, and then 0.8 mM TMB (Tetramethylbenzidine) solution was added thereto at 100 µl per well, to effect color development at 30° C. for five to 20 minutes (color reaction). 100 µl of 1.5 N $H_3PO_4$ was added to each well to stop the color reaction, and the absorbance at 450 nm was measured using a microtiter plate reader. According to the instructions provided by the manufacturer, the measured concentrations were calibrated using a lyophilized control reagent.

Figure 2:
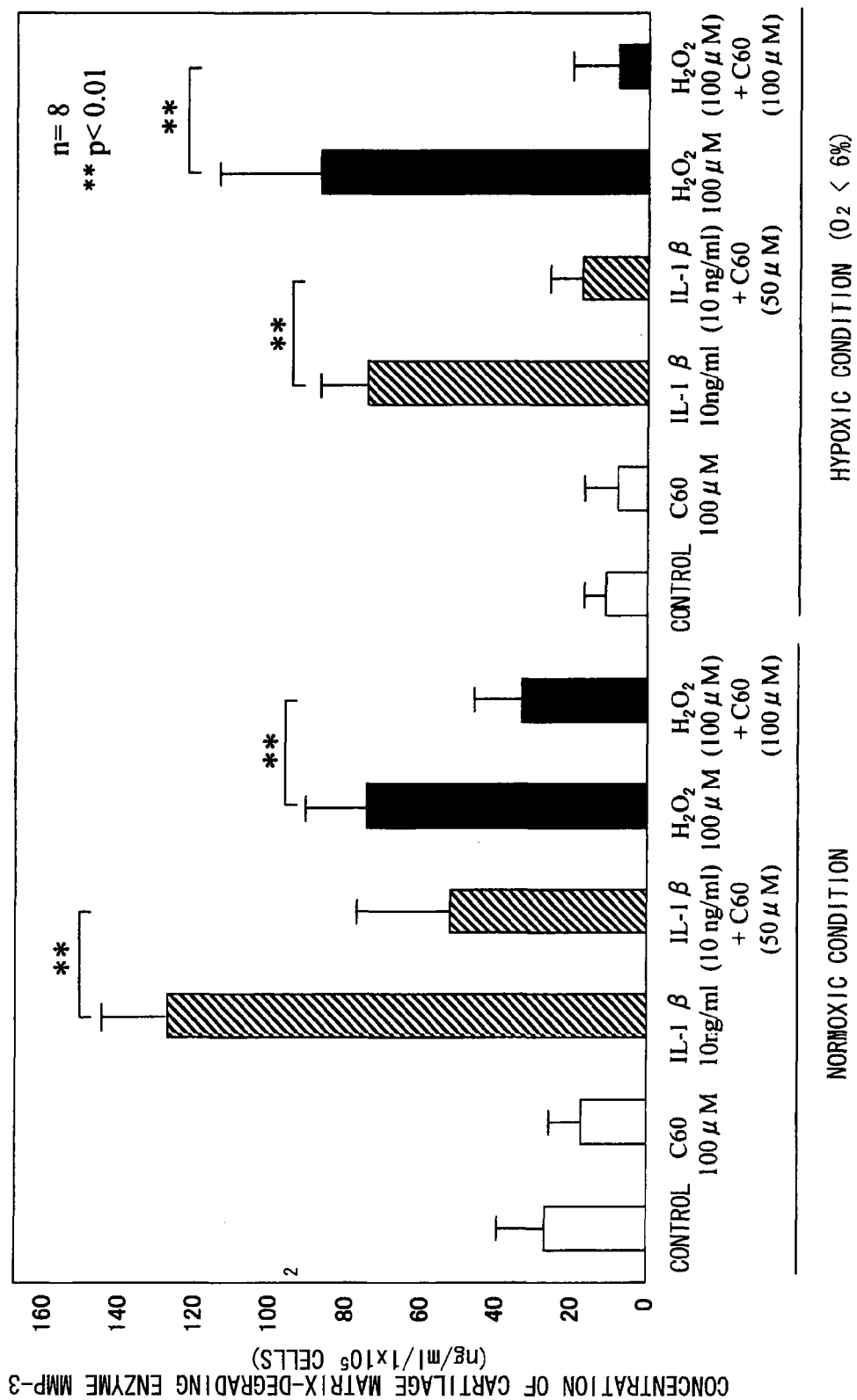
FIG. 2 is a histogram showing that the amount of produced cartilage-degrading enzyme MMP-3 differs depending on the presence/absence of fullerene when cultured chondrocytes are treated with a cartilage degenerating factor (IL-1β or $H_2O_2$). The addition of fullerene decreased the amount of MMP-3 produced, which had been increased by the cartilage degenerating factor.
Figure 3:
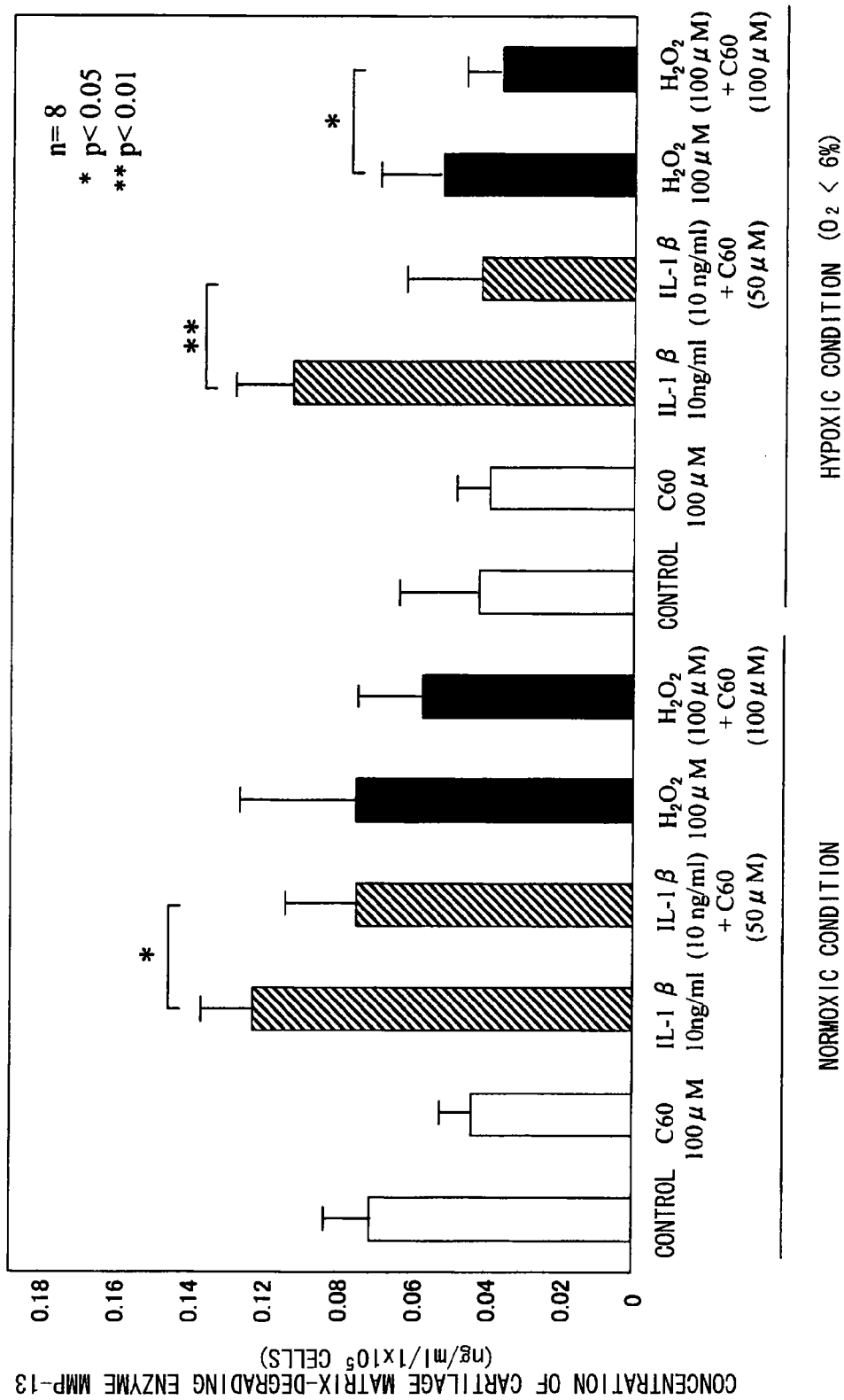
FIG. 3 is a histogram showing that the amount of produced cartilage-degrading enzyme MMP-13 differs depending on the presence/absence of fullerene when cultured chondrocytes are treated with a cartilage degenerating factor (IL-1β or $H_2O_2$). The addition of fullerene decreased the amount of MMP-13 produced, which had been increased by the cartilage degenerating factor.

FIGS. 1, 2, and 3 respectively show the measured results of MMP-1, 3, and 13. When cultured chondrocytes were cultured with the addition of a cartilage degenerating factor (IL-1β or $H_2O_2$), the production of the three types of the cartilage matrix-degrading enzymes (MMP-1, 3, and 13) was increased in all cases. Under the presence of hydroxylated C60 fullerene (50 or 100 µM), the production of these enzymes was inhibited in all cases. In particular, the inhibitory effect of hydroxylated C60 fullerene was also observed even under hypoxic condition that is close to that of cartilage tissue.

(4) Improving Effect of Hydroxylated Fullerene on Cartilage Matrix-Synthesizing Ability (i) Evaluation of Mitigating Effect of Hydroxylated Fullerene on Cartilage Matrix-production Ability using ELISA Method Influence of hydroxylated 60 fullerene on cartilage matrix (proteoglycan or type II collagen) production ability decreased by cartilage catabolism inducers was analyzed using ELISA.

Chondrocytes that had been isolated and cultured by the above method (1) were subjected to two secondary cultures. Then, these cells in a subconfluent state were disseminated into a 24 well-culture plate at $1 \times 10^5$ cells/well. After incubation for 12 hours, the wells were washed with PBS and the medium was replaced with a fresh 10% FBS-containing DMEM. A cartilage catabolism inducer (either 10.0 ng/ml interleukin (IL)-1β (purchased from Sigma), or 100 µM hydrogen peroxide solution ($H_2O_2$, purchased from Wako Pure Chemical Industries, Ltd.)) was then added to the cultured cells. 50.0 µM or 100.0 µM hydroxylated 60 fullerene was added in addition to the IL-1β or $H_2O_2$, and the plate was incubated for 24 hours. As controls, experiments of a group cultured in medium alone and groups cultured in medium added only with either (IL)-1β or hydrogen peroxide solution were also conducted in parallel. After a 24-hour incubation, the culture supernatant was collected.

The production quantities (concentrations) of the cartilage matrix (proteoglycan and type II collagen) in the culture supernatant were determined using ELISA kits (a kit for proteoglycan, manufactured by BioSource; and a kit for type II collagen, manufactured by Chondrex, Inc.), which is the standard technique currently known in the art.

Figure 4:
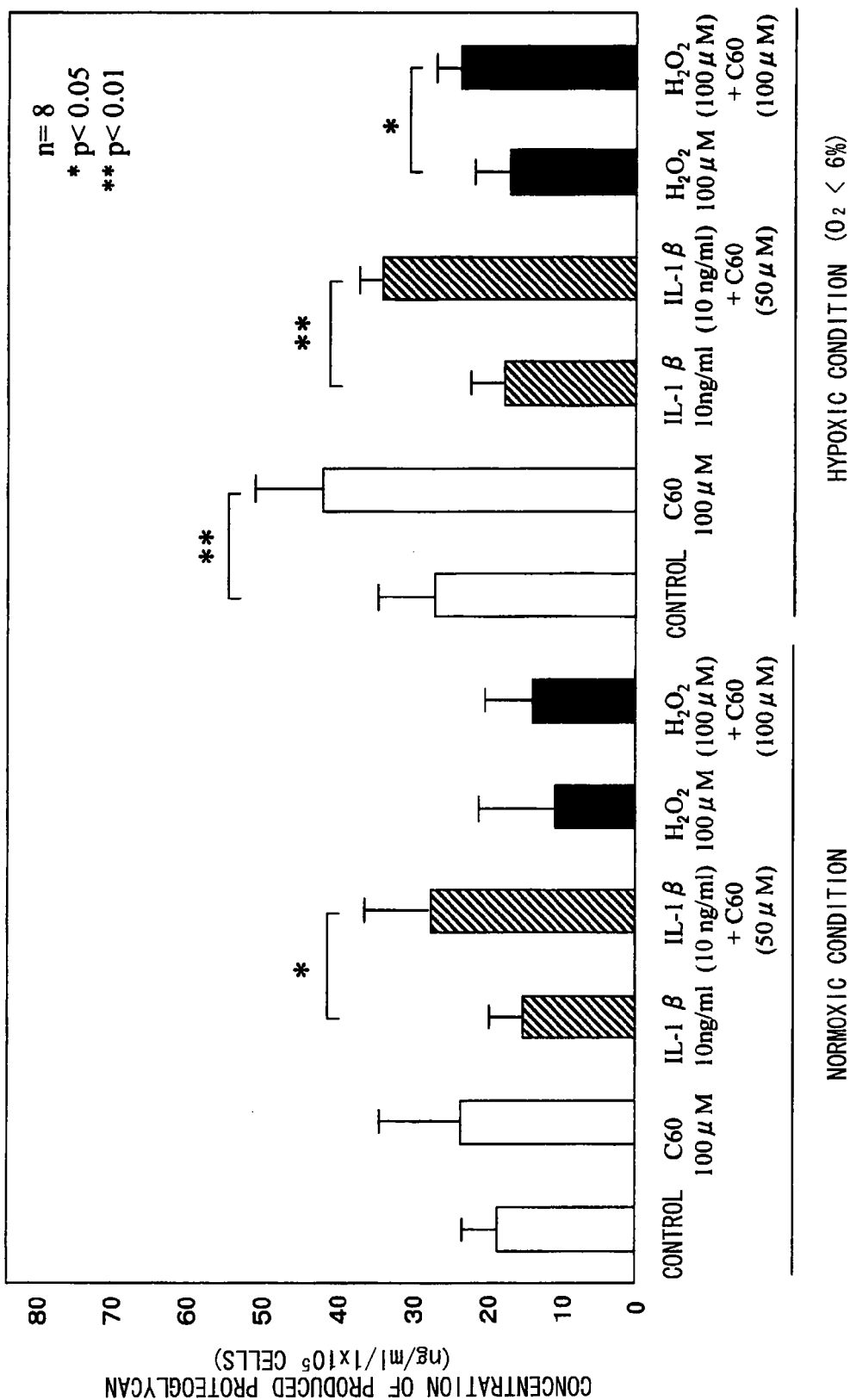
FIG. 4 is a histogram showing that the amount of synthesized cartilage matrix (proteoglycan) differs depending on the presence/absence of fullerene when cultured chondrocytes are treated with a cartilage degenerating factor (IL-1β or $H_2O_2$). The addition of fullerene restored cartilage matrix synthesis, which had been decreased by the cartilage degenerating factor.

As shown in FIG. 4, cartilage matrix (proteoglycan)-synthesizing ability was decreased by the addition of IL-1β or $H_2O_2$ which are cartilage degenerating factors for cultured chondrocytes. However, hydroxylated 60 fullerene (50 and 100 µM) was able to restore the decreased synthesizing ability due to these cartilage degenerating factors. Moreover, proteoglycan synthesizing ability of the group added with hydroxylated 60 fullerene alone was shown to be increased as compared to that of the control groups.

(ii) Evaluation of the Enhancing Effect of Hydroxylated 60 Fullerene on Cartilage Matrix-synthesizing Ability using Western Blotting Chondrocytes prepared according to the above method and chondrocytes of the control groups were collected with a cell scraper, and centrifuged to remove the supernatant. Then, 0.5% Triton X-100 aqueous solution was added thereto, and ultrasonic disintegration was performed on ice for one minute, to obtain a protein extract. The concentrations of the respective protein solutions were measured, and each sample was placed on 5% to 10% gradient SDS-polyacrylamide electrophoresis gel at 100 ng/lane, and subjected to electrophoresis.

Proteins in the gel were transferred onto a polyvinylidene difluoride membrane (manufactured by Pharmacia Co.) using a semidry blotting apparatus (manufactured by Amersham). The membrane was blocked with 5% skim milk (manufactured by Morinaga Co.), and then treated with 5 µg/ml of anti-proteoglycan monoclonal antibodies (manufactured by Chemicon Co.) at room temperature for one hour. The membrane was washed with PBS containing 0.01% Tween-20 (hereunder, abbreviated as "TPBS"), and then treated with 5,000-fold-diluted peroxidase-labeled anti-mouse IgG antibodies (manufactured by Amersham) as secondary antibodies, at room temperature for one hour. The membrane was again washed with TPBS, color was developed using an ECL western blotting kit. β-actin was also visualized in the same manner as an internal control for standardizing the protein amount at the time of preparation.

Figure 5:
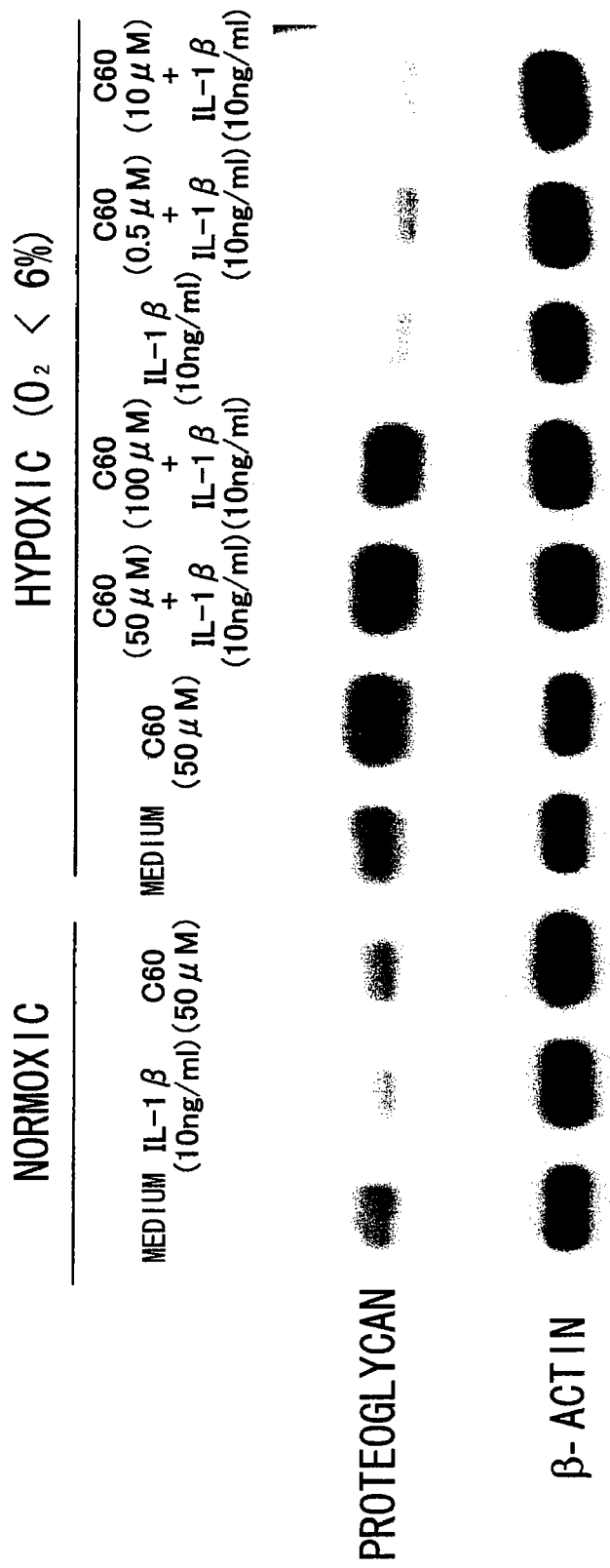
FIG. 5 is a photograph showing the results of measuring, by western blotting, the amount of proteoglycan produced in cultured chondrocytes after being treated with a cartilage degenerating factor. Amount of synthesized proteoglycan was shown to be restored by the addition of fullerene together with the cartilage degenerating factor.

As shown in FIG. 5, the results of western blotting were similar to those of the proteoglycan measurement using ELISA described above. That is, the inhibition against the production of cartilage matrix, proteoglycan, due to the cartilage degenerating factors was inhibited by the addition of hydroxylated C60 fullerene.

Example 2

Inhibition of Cartilage Degeneration by Fullerene using Osteoarthritis Model Rabbits whose Knee Joint Ligaments were Excised (1) Preparation of Osteoarthritis (Cartilage Degeneration) Rabbit Model Osteoarthritis animal model was prepared according to a general method. NZW-strain male rabbits (2 to 2.5 kg, purchased from Kitayama Labes Co.) were habituated for about one week, and both knee joint sites were shaved and disinfected with an iodine antiseptic agent under anesthesia with a combined administration of ketamine hydrochloride and xylazine (intramuscular administration, or intravenous administration if the anesthetic effect was low). The epidermis inside the knee joints was incised to expose the anterior cruciate ligament and medial collateral ligament, which were then cut out. After confirming and incising the articular capsule, the medial meniscus was exposed and totally extracted. Tissues around the articular capsule, patellar tendon, and epidermis were sutured thereafter. At the time of suturing, the operated site was washed with a physiological salt solution containing an antibiotic (injectable Viccillin, Meiji Seika) (500 mg (titer) as ampicillin sodium/20.0 ml of physiological saline solution). The incision of the anterior cruciate ligament and the medial collateral ligament, and the total extraction of the medial meniscus and the like would cause oxidative stress involved with trauma in the rabbit joints, and symptoms of osteoarthritis would appear.

Meanwhile, the operation of the sham operation group was merely a skin incision followed by suturing.

(2) Inhibitory Effect of Hydroxylated C60 Fullerene on Rabbit Knee Articular Cartilage Degeneration From the postoperative first week, 2.0 ml of a hydroxylated C60 fullerene solution (100 µM, adjusted with the solvent polyethylene glycol) was injected into the right knee joint cavity, and 2.0 ml of solvent alone was injected into the left knee joint cavity, using a 23-gauge injection needle intraarticularly twice a week. On the postoperative zeroth, second, fourth, sixth, and eighth week, the rabbits were euthanatized by overdosing pentobarbital sodium, and then eight knee joints (left and right hind paw knee joints) were collected from four rabbits in each group. The collected knee joints were fixed with a 4% paraformaldehyde solution and then decalcified, from which paraffin embedded sections were prepared. The sections were stained with hematoxylin-eosin or safranin O, treated in an ethanol dehydration system, cleared in xylene, and then sealed with Canada balsam. The obtained sections were observed under an optical microscope to histologically analyze articular degeneration. Thickness of the degenerated cartilage layer and the number of chondrocytes in the degenerated cartilage layer were measured. The thickness of the degenerated cartilage layer was expressed as a relative value assuming that the immediate postoperative thickness (zeroth week) was 100%.

Moreover, proteoglycan content decrease in articular cartilage involved with cartilage degeneration was evaluated by safranin O staining. The evaluation result was expressed as an area ratio (%) to immediate postoperative proteoglycan-stained area.

TABLE 2

Change in degree of cartilage degeneration with time in rabbit model for osteoarthritis

| Postoperative | $2^{nd}$ week | | $4^{th}$ week | | $6^{th}$ week | | $8^{th}$ week | |
| --- | --- | --- | --- | --- | --- | --- | --- | --- |
| | Left knee (group administered with solvent alone) | Right knee (group administered with 100 µM fullerene) | Left knee (group administered with solvent alone) | Right knee (group administered with 100 µM fullerene) | Left knee (group administered with solvent alone) | Right knee (group administered with 100 µM fullerene) | Left knee (group administered with solvent alone) | Right knee (group administered with 100 µM fullerene) |
| Thickness of degenerated cartilage layer (percentage to immediate postoperative thickness) | 98 ± 11 | 99 ± 4 | 75 ± 7 | 94 ± 6 | 52 ± 10 | 84 ± 11 | 42 ± 14 | 76 ± 9 |
| | | | * | | ** | | ** | |

TABLE 2-continued

Change in degree of cartilage degeneration with time in rabbit model for osteoarthritis

| Postoperative | 2nd week | | 4th week | | 6th week | | 8th week | |
|---|---|---|---|---|---|---|---|---|
| | Left knee (group administered with solvent alone) | Right knee (group administered with 100 μM fullerene) | Left knee (group administered with solvent alone) | Right knee (group administered with 100 μM fullerene) | Left knee (group administered with solvent alone) | Right knee (group administered with 100 μM fullerene) | Left knee (group administered with solvent alone) | Right knee (group administered with 100 μM fullerene) |
| Number of chondrocytes in the degenerated cartilage part (optical microscopy at 200x magnification, number of cells/view field of 0.785 cm$^2$) | 24 ± 8 | 28 ± 6 | 16 ± 5 | 21 ± 4 * | 7 ± 4 | 18 ± 6 ** | 3 ± 2 | 16 ± 9 ** |
| Degree of safranin O staining in the degenerated cartilage part (area ratio (%) to immediate postoperative proteoglycan-stained area) | 96 ± 6 | 102 ± 7 | 68 ± 10 | 85 ± 7 * | 30 ± 12 | 72 ± 9 ** | 8 ± 4 | 65 ± 9 ** |

* $p < 0.05$, ** $p < 0.01$

As shown in Table 2, progress of cartilage degeneration was observed with time from the postoperative second week in the knee joint cartilage of the group administered with solvent alone. In contrast, in the knee joint cartilage tissue of the group administered with hydroxylated C60 fullerene, degeneration of the cartilage tissue was mild, and the chondrocytes and the cartilage matrix were histologically maintained at the time point of postoperative sixth and eighth week.

Intraarticular injection of polyethylene glycol (2.0 ml) alone had no influence on the natural course of cartilage degeneration.

Moreover, although data is not shown, during the period of the animal experiment (intraarticular injection), neither swelling/flare in articular local parts nor influence on systemic condition was observed in both groups, the group administered with solvent alone and the group administered with hydroxylated C60 fullerene.

From the above results, hydroxylated C60 fullerene was revealed to have a potential to inhibit cartilage degeneration.

Accordingly, the hydroxylated C60 fullerene formulation is useful as a therapeutic agent for osteoarthritis (cartilage degeneration).

(3) Examination of Inhibitory Effect of Intraarticular Injection with Various Concentrations (0.1 to 40.0 μM) of Water-Solubilized Fullerene on Articular Cartilage Degeneration Various concentrations (0.1, 1.0, 10.0, or 40.0 μM) of water-solubilized fullerene (cyclodextrin clathrate C60) was injected into the right knee joints of osteoarthritis model animals (rabbits), and solvent alone was injected into the left knee joints as controls intraarticularly once a week. On the fourth or eighth week after the start of administration, the knees were dissected and stained with safranin O, to compare the degree of cartilage degeneration of medial and lateral tibia.

In both a four-week administration and an eight-week administration, the inhibitory effect on articular cartilage degeneration was confirmed at the respective concentrations. The result of the eight-week administration is shown in Table 3.

TABLE 3

| Postoperative | 0.1 μM test | | 1.0 μM test | | 10.0 μM test | | 40.0 μM test | |
|---|---|---|---|---|---|---|---|---|
| | Control left knee (group administered with solvent alone) | Right knee (group administered with 0.1 μM fullerene) | Control left knee (group administered with solvent alone) | Right knee (group administered with 1.0 μM fullerene) | Control left knee (group administered with solvent alone) | Right knee (group administered with 10.0 μM fullerene) | Control left knee (group administered with solvent alone) | Right knee (group administered with 40.0 μM fullerene) |
| Thickness of degenerated cartilage layer (percentage to immediate postoperative mean thickness) | 55 ± 10 | 60 ± 9 | 49 ± 9 | 62 ± 8 * | 52 ± 11 | 67 ± 8 * | 57 ± 6 | 66 ± 7 |
| Number of chondrocytes in the degenerated cartilage part (optical microscopy at 200x magnification, number of cells/view field of 0.785 cm$^2$) | 12 ± 5 | 22 ± 9 * | 15 ± 11 | 25 ± 6 ** | 11 ± 6 | 20 ± 7 ** | 14 ± 8 | 26 ± 9 ** |
| Degree of safranin O staining in the degenerated cartilage part (area ratio (%) to immediate postoperative mean proteoglycan-stained area) | 35 ± 13 | 47 ± 14 * | 22 ± 11 | 44 ± 10 ** | 24 ± 12 | 48 ± 7 ** | 28 ± 11 | 45 ± 12 ** |

* $p < 0.05$, ** $p < 0.01$

As shown in Table 3, the eight-week administration with water-solubilized fullerene showed a mild efficacy in all four rabbits in the 0.1 μM administered group; a moderate efficacy in two rabbits and a remarkable efficacy in one rabbit out of a total of four in the 1.0 μM administered group; a remarkable efficacy in three rabbits out of a total of four in the 10.0 μM administered group; and a mild efficacy in one rabbit and moderate efficacy in another rabbit out of a total of three in the 40.0 μM administered group. In particular, in the eight-week administration, the inhibitory effect of water-solubilized fullerene on cartilage degeneration was more remarkable in the 1.0 μM and 10.0 μM administered groups rather than the 0.1 μM administered group. This result is noteworthy considering that the cartilage degeneration inhibitory effect was almost equivalent throughout the 0.1 μM to 40 μM administered groups in the four-week administration (the result is not shown). During the eight-week test period, decrease in body weight, insufficient feeding, hematuria, or abnormal hair coat was not observed in the experimental animals. In the optical microscopic observation of organs other than the joints (such as brain, lung, liver, kidney, adrenal, and testis), no findings showing degeneration in the respective tissues was observed.

Sequential biochemical examinations of blood and synovial fluid were also performed (pre-administration and fourth- and eighth-week post-administration of water-solubilized fullerene). The observed biochemical examination items were (A) hepatic function (GOT and GPT), renal function (urea nitrogen and creatinine), and electrolytes (Na, K, and Cl), (B) extracellular matrix-degrading enzyme production ability (MMP-1, 3, and 13), and (C) cartilage matrix-synthesizing ability (proteoglycan). The items of (A) were measured by commercially available testing equipments and items of (B) and (C) were measured by ELISA method.

The hepatic function, the renal function, and the electrolyte balance were not significantly changed at respective time points of pre-administration and fourth- and eighth-week post-administration.

Figure 6:
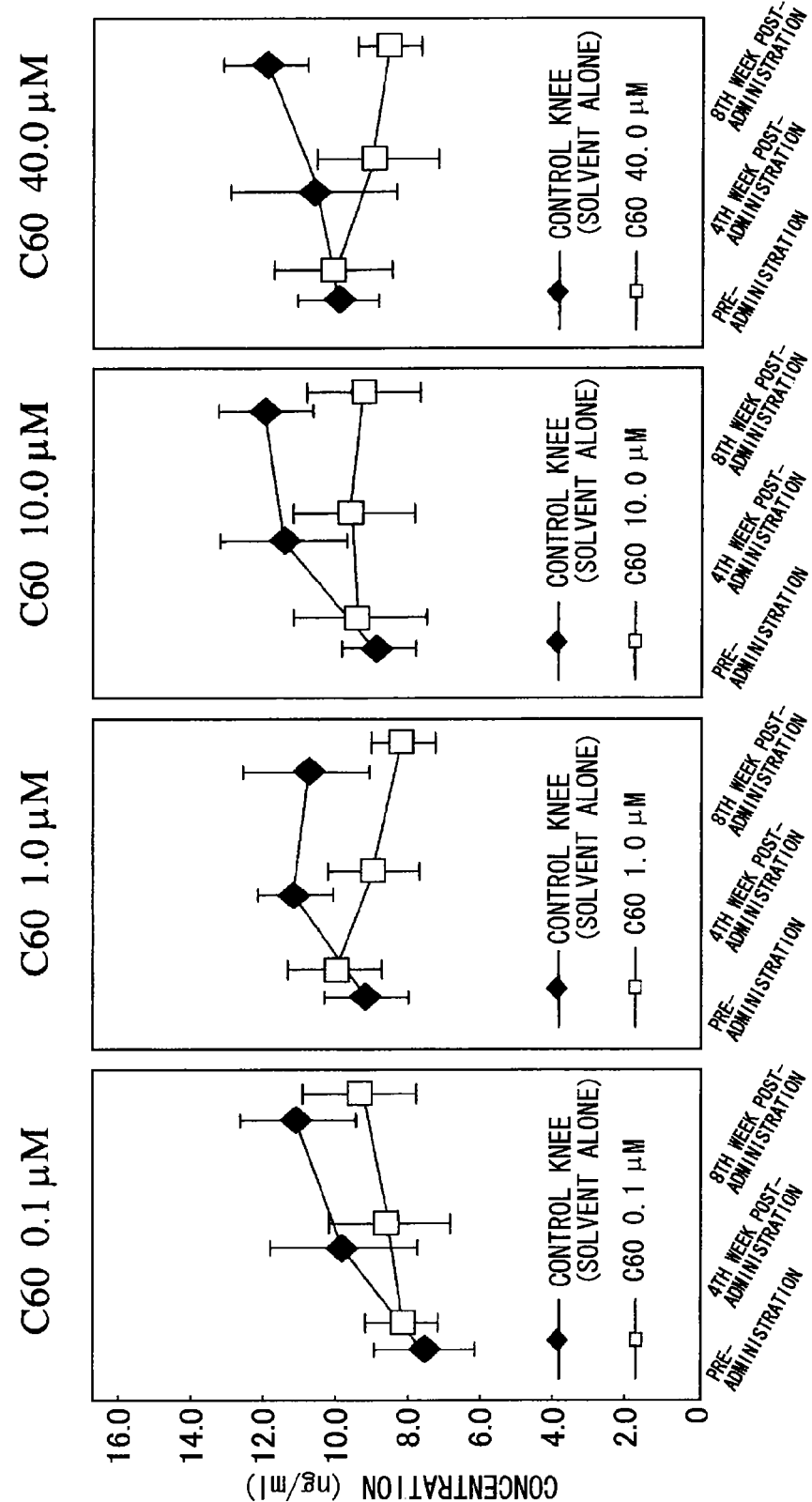
FIG. 6 depicts the results of a sequential measurement of MMP-1 concentration in synovial fluid of the knee joints of osteoarthritis model (rabbit) administered with various concentrations of hydroxylated C60 fullerene or a control. The MMP-1 concentration in the control knees showed an increasing tendency with time, whereas a MMP-1 production inhibitory effect was observed in the knees administered with hydroxylated C60 fullerene.
Figure 7:
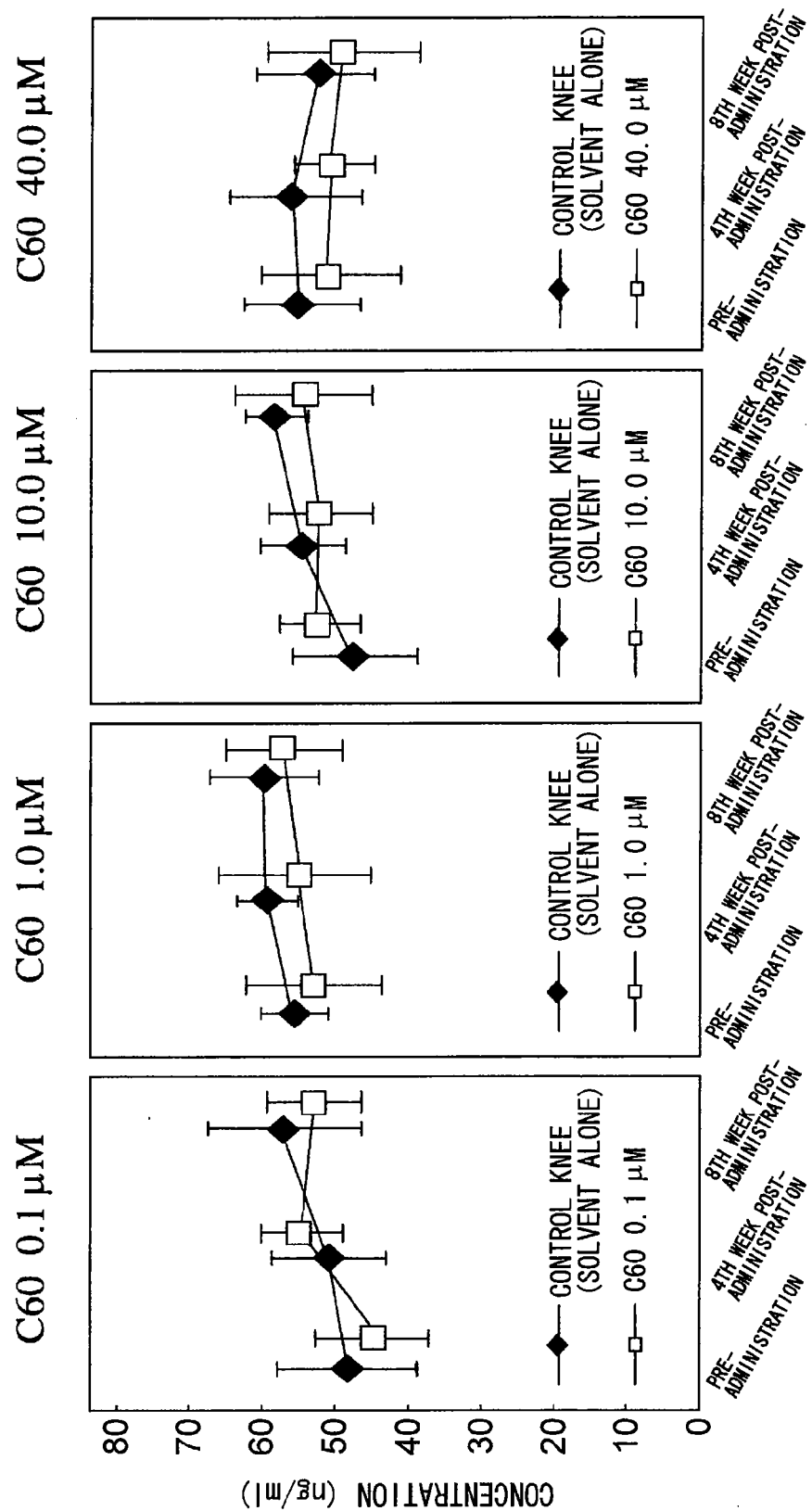
FIG. 7 depicts the results of a sequential measurement of MMP-3 concentration in synovial fluid of the knee joints of osteoarthritis model (rabbit) administered with various concentrations of hydroxylated C60 fullerene or a control. No remarkable difference in MMP-3 concentration was observed between the control knees and the knees administered with hydroxylated C60 fullerene.
Figure 8:
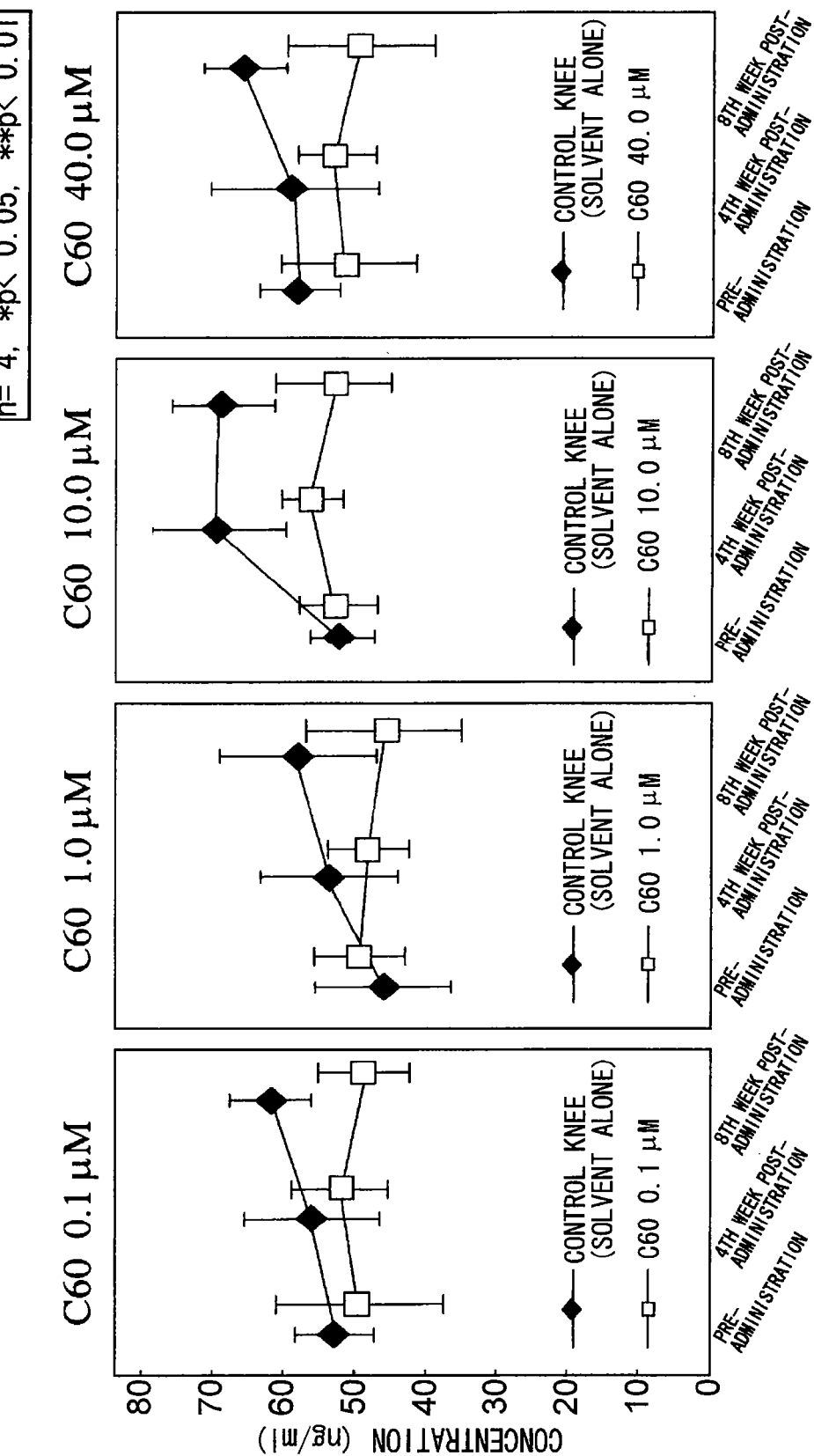
FIG. 8 depicts the results of a sequential measurement of MMP-13 concentration in synovial fluid of the knee joints of osteoarthritis model (rabbit) administered with various concentrations of hydroxylated C60 fullerene or a control. The MMP-13 concentration in the control knees showed an increasing tendency with time, whereas a MMP-13 production inhibitory effect was observed in the knees administered with hydroxylated C60 fullerene.

The concentrations of MMP-1, 3, and 13, and proteoglycan in blood serum were under the detection limit. Influence of the administration with water-solubilized fullerene on the concentrations of MMP-1 and MMP-13 in the synovial fluid was observed (FIGS. 6 and 8). Influence of the administration with water-solubilized fullerene on the concentrations of MMP-3 and proteoglycan in the synovial fluid was not clear (FIG. 7).

As described above, the therapeutic effect of the four-week or eight-week repetitive administration with water-solubilized fullerene was confirmed. Therefore, the therapeutic effect of a single administration of water-solubilized fullerene was also examined. Immediately after the preparation of an osteoarthritis rabbit model, a single dose of water-solubilized fullerene was administered. On the eighth week, articular cartilage tissue samples were prepared, and the therapeutic effect was examined. As a result, no clear inhibitory effect on cartilage degeneration was observed as compared with the control knees in the single administration.

(4) Comparative Test of the Medicinal Effect Between Water-Solubilized Fullerene and a Known Articular Function-Improving Agent The medicinal effect of water-solubilized fullerene (cyclodextrin clathrate C60) was examined comparatively with a known articular function-improving agent (the hyaluronic acid formulation Suvenyl (registered trademark)). Specifically, the effects at the eighth week after the start of treatment on rabbits in the following five groups (A) to (E) were examined. Each group consisted of four rabbits and the administration dosage was 2.0 ml/rabbit in all groups.

Test groups: (A) Sham-operation, group administered with Suvenyl; (B) Sham-operation, group administered with 50% polyethylene glycol; (C) Osteoarthritis model, group administered with 1.0 μM water-solubilized fullerene; (D) Osteoarthritis model, group administered with 50% Suvenyl; (E) Osteoarthritis model, group administered with 1.0 μM water-solubilized fullerene and Suvenyl.

Figure 9:
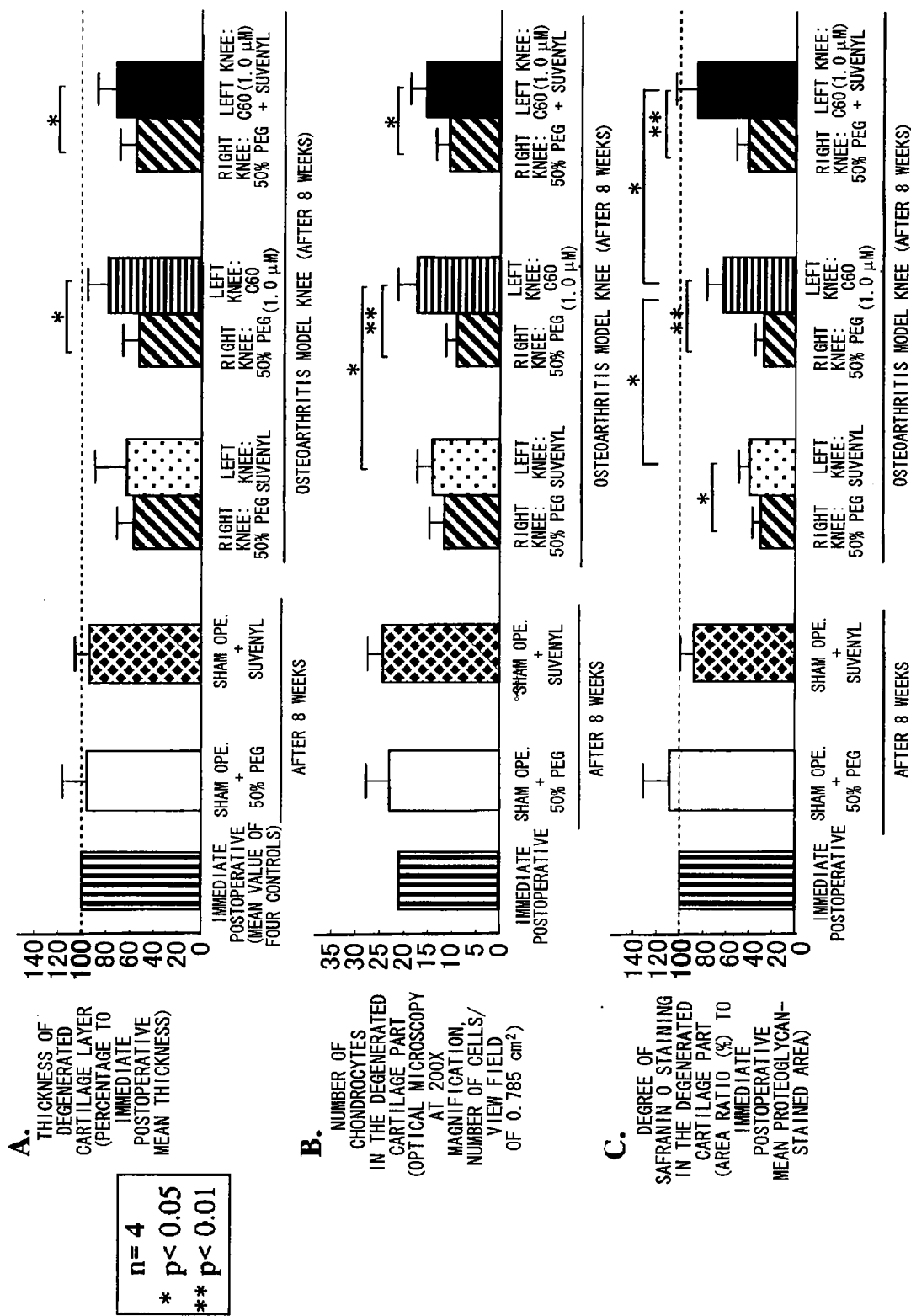
FIG. 9 depicts the results of comparing the therapeutic effect of hydroxylated C60 fullerene with that of hyaluronic acid formulation, using the osteoarthritis model (rabbit).

The results are shown in FIG. 9. Water-solubilized fullerene showed more remarkable effects than the hyaluronic acid formulation on both the inhibitory effect on the production of cartilage matrix-degrading enzymes (MMPs) and the producing/maintaining effect of proteoglycan.

Example 3

Examination of Lubricating Effect of Fullerene

Lubricating effect of fullerene was examined using three different solutions. 20 ml each of the solutions of (A) osteoarthritis patient-derived synovial fluid, (B) 50% polyethylene glycol solution, and (C) joint function-improving agent (hyaluronic acid formulation) were prepared, and dispensed into two tubes at 10 ml each. One 10 ml solution was mixed with fullerene (C60) to adjust the final concentration to 1.0 μM. The other 10 ml solution was used as a control solution. The dynamic friction coefficients of the respective solutions at room temperature were measured three times by a pendulum-type dynamic friction coefficient measuring apparatus (Japan Lubricating Oil Society), and the mean values were calculated. The dynamic friction coefficients were compared between the fullerene solutions and the control solutions.

As a result, in all three types of above solutions, dynamic friction coefficient showed a decreasing tendency due to the mixing of fullerene (Table 4).

TABLE 4

| | Dynamic friction coefficient | Friction coefficient decreasing rate to control solution |
|---|---|---|
| A. | | |
| Control solution (osteoarthritis patient-derived synovial fluid alone) | 0.166 | 37% |
| Synovial fluid + C60 (1 μM) | 0.111 | |
| B. | | |
| Control solution (50% polyethylene glycol alone) | 0.139 | 25% |
| 50% polyethylene glycol + C60 (1 μM) | 0.104 | |
| C. | | |
| Control solution (hyaluronic acid formulation) | 0.199 | 42% |
| Hyaluronic acid formulation + C60 (1 μM) | 0.116 | |

As described above, low friction of articular cartilages and lubricating ability of synovial fluid were improved by the injection of fullerene into a joint, suggesting that fullerene has an inhibitory effect on articular cartilage degeneration.

INDUSTRIAL APPLICABILITY

The present invention's agents comprising fullerenes inhibit cartilage matrix-degrading enzyme production induced by oxidative stress, cartilage degenerating factors, and the like, improve cartilage matrix-synthesizing ability, and improve low friction of articular cartilage and lubricating ability of synovial fluid. Moreover, the present invention is also useful as novel therapeutic agents for motor organ diseases involving cartilage degeneration caused by oxidative stress and the like, for example, osteoarthritis.

The invention claimed is:

1. A method for treating cartilage degeneration, comprising intraarticularly administering in a subject in need thereof a pharmaceutically effective amount of at least one active ingredient selected from the group consisting of an un-substituted fullerene, a clathrate fullerene, a heterofullerene, a norfullerene, a homofullerene, a secofullerene, a fullerene polymer, a chemically modified fullerene selected from the group consisting of a hydrogenated fullerene, a fullerene substituted with a hydroxyl group, an amino group, or a carboxyl group, and a fullerene conjugated with polyethylene glycol or hyaluronic acid, and a salt thereof, wherein the dosage is 0.1 micro Molar to 100 micro Molar per affected part, and wherein the active ingredient induces cartilage matrix production.

2. The method of claim 1, wherein the active ingredient is C60 fullerene.

3. The method of claim 1, wherein the active ingredient is hydroxylated C60 fullerene.

4. The method of claim 1, wherein the cartilage degeneration is caused by oxidative stress.

5. The method of claim 1, wherein the cartilage degeneration is osteoarthritis.

6. The method of claim 1, wherein the active ingredient inhibits production of a cartilage matrix-degrading enzyme.

7. The method of claim 6, wherein the cartilage matrix-degrading enzyme is a matrix metalloprotease induced by a cartilage degenerating factor in a chondrocyte.

8. The method of claim 6, wherein the cartilage matrix-degrading enzyme is MMP-1, 3, and/or 13.

9. The method of claim 1, wherein the active ingredient induces cartilage matrix production which has been decreased by a cartilage degenerating factor in a chondrocyte.

10. The method of claim 1, wherein the cartilage matrix is proteoglycan and/or type II collagen.

* * * * *

UNITED STATES PATENT AND TRADEMARK OFFICE
CERTIFICATE OF CORRECTION

| | | |
|---|---|---|
| PATENT NO. | : 8,395,037 B2 | Page 1 of 1 |
| APPLICATION NO. | : 11/909264 | |
| DATED | : March 12, 2013 | |
| INVENTOR(S) | : Yudoh | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1185 days.

Signed and Sealed this
Second Day of December, 2014

Michelle K. Lee
*Deputy Director of the United States Patent and Trademark Office*